(12) United States Patent
Pan (10) Patent No.: US 10,204,840 B2
(45) Date of Patent: Feb. 12, 2019

(54) METHOD FOR MEASURING GAS DISSOCIATION DEGREES

(71) Applicant: Jui-Pao Pan, Hsinchu (TW)

(72) Inventor: Jui-Pao Pan, Hsinchu (TW)

(73) Assignee: FairTech Corporation, Hsinchu (TW)

( * ) Notice: Subject to any disclaimer, the term of this patent is extended or adjusted under 35 U.S.C. 154(b) by 0 days.

(21) Appl. No.: 15/606,809

(22) Filed: May 26, 2017

(65) Prior Publication Data

US 2018/0190548 A1 Jul. 5, 2018

(30) Foreign Application Priority Data

Jan. 5, 2017 (TW) .............................. 106100285 A (51) Int. Cl.
*G01N 21/85* (2006.01)
*H01L 21/66* (2006.01)
*G01N 21/94* (2006.01)
*G01N 21/84* (2006.01)

(52) U.S. Cl.
CPC .............. *H01L 22/26* (2013.01); *G01N 21/85* (2013.01); *G01N 21/94* (2013.01); *G01N 2021/8416* (2013.01); *G01N 2021/8578* (2013.01)

(58) Field of Classification Search
CPC ......... H01L 22/26; G01N 21/68; G01N 21/69
See application file for complete search history.

(56) References Cited

U.S. PATENT DOCUMENTS

2005/0195393 A1* 9/2005 Karanassios ........... G01N 21/67
356/316

* cited by examiner

*Primary Examiner* — Kyoung Lee (57) ABSTRACT

A method for measuring gas dissociation degrees is provided. The method comprises the following steps. A reaction process with at least one reactive gas in a main path and a second path connecting to the main path is performed. A plasma gas dissociation degree of the reactive gas in the reaction process is detected. A dissociation quantity value of the reactive gas in the reaction process is calculated. An amount of the reactive gas in the main path after the reaction process is provided. The reactive gas is discharged according to the dissociation quantity value of the reactive gas for removing contaminants in the main path.

14 Claims, 9 Drawing Sheets

METHOD FOR MEASURING GAS DISSOCIATION DEGREES

BACKGROUND OF THE INVENTION

1. Field of the Invention

The present invention provides a method and a device for measuring gas dissociation degrees with an optical spectrometer. In current application of gas, the dissociation degree in some special gas is generally detected and controlled by a physical or chemical method instead of an optical one. Solution schemes that are typically adopted include but are not limited to adjusting gas flow rates, gas proportioning or gas disposal. But up to now there has not been any definitively effective solution scheme. Rather than adopting the above-mentioned methods, the present invention monitors gas dissociation degrees by using spectroscopy. A primary objective of the present invention is to provide a method and a device for measuring gas dissociation degrees, wherein the gas dissociation degree in a tube body is detected by a device according to the present invention and the relative dissociation quantity value is calculated to serve as a reference for choosing among various corresponding handling methods. For example, an appropriate amount of dissociated reactive gas may be discharged to remove contaminants in a primary path of gas to achieve efficient and effective cleaning. The principle of the present invention is to detect the gas dissociation degree in a tube body and to calculate the relative dissociation quantity value by means of a device according to the present invention. When the contamination value in a primary path of gas is too high, an appropriate amount of dissociated reactive gas may be discharged in a second path for removing contaminants in the primary path to achieve efficient and effective cleaning. The primary path and the second path connected to the primary path are provided for storing reactive gas. The primary path is provided to perform the processes of plasma-assisted deposition, membrane etching and material surface modification to achieve special functions and effects. As a location therefrom gas dissociation degrees may be measured may be varied, a measuring method and a device according to the present invention may be applied in various locations for measuring gas dissociation degrees and are not limited to the chamber referred to in the preferred embodiments below. Any location where a gas dissociation degree measuring device is disposed is within the scope of the present invention (referring to FIG. 1). The preferred embodiments below are illustrated of the present invention rather than limiting of the present invention, citing devices for physical vapor deposition, chemical vapor deposition or etching in the semiconductor industry as examples.

2. Description of Related Art

Plasma is a state of matter consisting mainly of free electrons and charged ions. It widely exists in the universe and is often considered as the fourth state of matter, being called plasmoid or ultragaseous state. Plasma is ion gas consisting of equal numbers of positive and negative electric charges. More specifically defined, plasma is quasi-neutral gas consisting of charged and neutral particles, and plasma is the collective behavior of these particles. A plasma source platform provides neutral active species generated in steadily supplied raw gas for the processes of surface modification, reaction chamber cleaning, membrane etching and plasma-assisted deposition.

Figure 2:
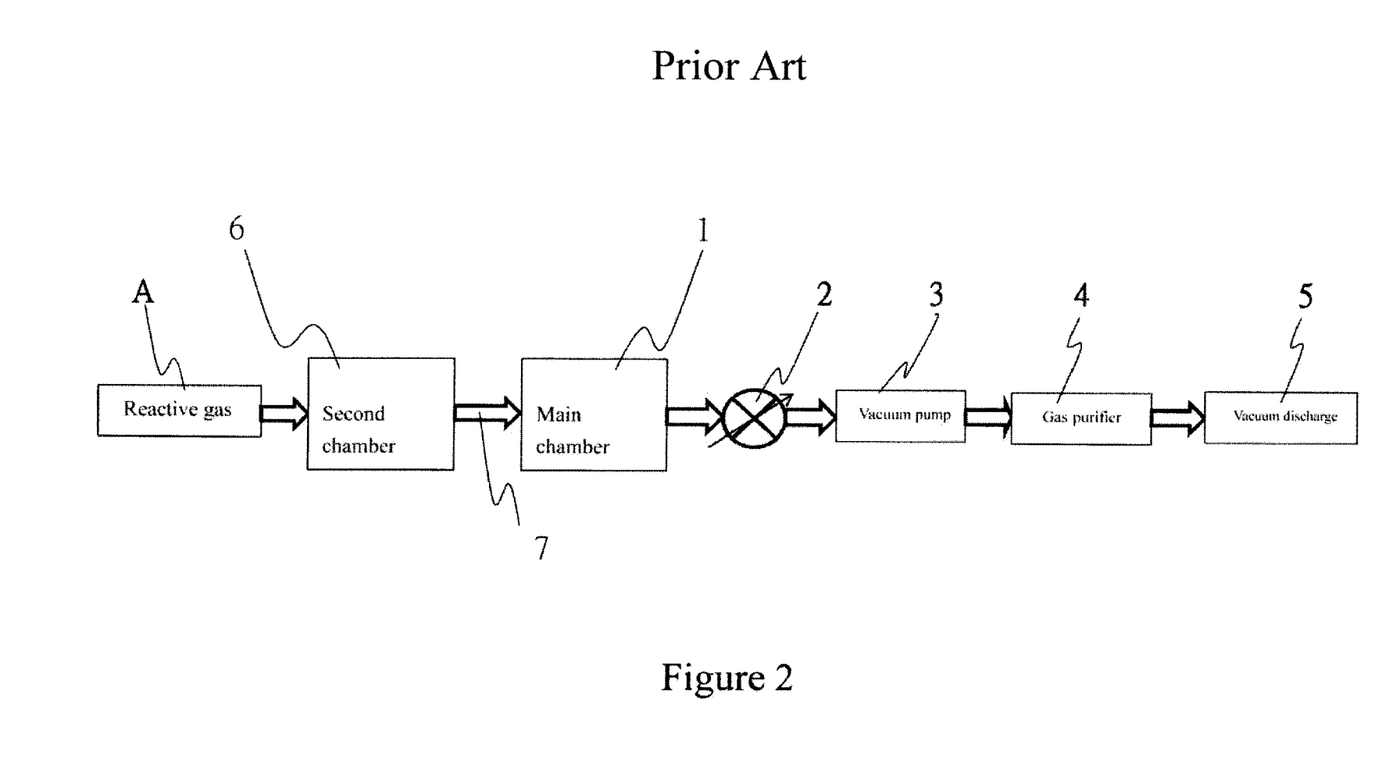
FIG. 2 is a block diagram of a conventional plasma gas device.

As FIG. 2 shows, a conventional plasma cleaning manufacturing process employs a main chamber 1 and a throttling valve 2, a vacuum pump 3 and a gas purifier 4 that are connected to the main chamber 1. After reactive gas A is fed, an appropriate amount of the reactive gas A is dissociated in a second chamber 6. Next the reactive gas A passes a tube body 7 and performs cleaning in the main chamber 1. Vacuum discharge 5 is then achieved by the vacuum pump 3 and gas purifier 4. After the foregoing process is performed over a period of time, plasma deposition may also remain on the wall surfaces of the main chamber 1 and contaminate the main chamber 1. In current practice, the main chamber 1 is cleaned manually. After cleaning an integrated circuit wafer probe is placed in the main chamber 1 for testing. If the testing result is dissatisfactory, further cleaning of the chamber 1 is required. This requires a lot of time and work, and having to repeatedly place an integrated circuit wafer probe in the main chamber 1 also increases labor and material costs. Therefore, in current practice, a second chamber 6 is connected to the main chamber 1 with a tube body 7 for storing gas in plasma state. When the main chamber 1 is contaminated, an appropriate reactive gas A is dissociated in the second chamber 6 and passed through the tube body 7 to perform cleaning of the main chamber 1. However, there is no way of knowing how much reactive gas A has to be dissociated in the second chamber 6 to effectively accomplish the cleaning of the main chamber 1. Therefore, after repeating the cleaning process of the main chamber 1 by dissociating an appropriate amount of reactive gas A in the second chamber 6 and passing it through the tube body 7 to perform cleaning of the main chamber 1, manual cleaning is still required and an integrated circuit wafer probe is placed in the main chamber 1 afterwards for testing to check whether further cleaning is necessary. Although the use of reactive gas A is an improvement upon manual cleaning, there is still need to repeatedly place an integrated circuit wafer probe in the main chamber 1 for testing, which increases labor and material costs. In view of this, after laborious research and experiments, the applicant has devised a method and a device for measuring gas dissociation degrees (including but not limited to plasma gas dissociation degrees) with an optical spectrometer to achieve more efficient and effective cleaning of the main chamber 1 at reduced labor and material costs.

SUMMARY OF THE INVENTION

It is a primary objective of the present invention to provide a method and a device for measuring gas dissociation degrees with an optical spectrometer, wherein the plasma gas dissociation degree in a tube body 7 is detected by a detecting element 8 and the relative dissociation quantity value is calculated based on which an appropriate amount of dissociated reactive gas A is discharged in a second chamber 6 to remove contaminants in the main chamber 1 to achieve more efficient and effective cleaning of the main chamber 1 at reduced labor and material costs.

A foregoing method and a device for measuring gas dissociation degrees with an optical spectrometer detects the plasma gas dissociation degree in a tube body 7 and calculates the relative dissociation quantity value by means of an optical spectrometer. When the contamination value in the main chamber 1 is too high, an appropriate amount of dissociated reactive gas A is discharged in a second chamber 6 for removing contaminants in the main chamber 1 to achieve efficient and effective cleaning. The main chamber 1 and the second chamber 6 connected to the main chamber 1 are provided for storing reactive gas A. The main chamber 1 is provided for performing the processes of plasma-assisted deposition, membrane etching and material surface modification to achieve special functions and effects in semiconductor integrated circuit manufacturing. The detecting element 8 and optical spectrum plasma gas dissociation measuring device 9 are disposed between the main chamber 1 and the second chamber 6.

A foregoing method and a device for measuring gas dissociation degrees with an optical spectrometer, wherein the main chamber 1 is connected to the second chamber 6 with a tube body 7 and the detecting element 8 is disposed at an appropriate location in the tube body 7.

In current application of gas, the dissociation degree in some special gas is generally detected and controlled by a physical or chemical method instead of an optical one. Solution schemes that are adopted include but are not limited to adjusting gas flow rates, gas proportioning or gas disposal. But up to now there has not been any definitively effective solution scheme. A primary objective of the present invention is to provide a method and a device for measuring gas dissociation degrees. The principle of the present invention is to detect the gas dissociation degree in a tube body and to calculate the relative dissociation quantity value by means of a device according to the present invention. When the contamination value in a primary path of gas is too high, an appropriate amount of dissociated reactive gas is discharged via a second path to remove contaminants in the primary path to achieve efficient and effective cleaning. The primary path and the second path connected to the primary path are provided for storing reactive gas. The primary path is provided to perform the processes of plasma-assisted deposition, membrane etching and material surface modification to achieve special functions and effects. The present invention may be applied to any device and/or any apparatus that requires measuring of gas dissociation degrees, including but not limited to physical vapor deposition device, chemical vapor deposition device, etching device and any other relevant device in the semiconductor, photoelectric, panel industries and any other relevant industry. The present invention may also be directly disposed in a remote plasma source device. Further, the present invention may be applied in any inspection examination device in the biotechnology, chemistry, applied physics industries and any other relevant industry. Still further, the present invention may be applied to any inspection apparatus or testing platform in the equipment maintenance industry for any of the foregoing industries. A measuring method and a device according to the present invention may be applied in various locations for measuring gas dissociation degrees and are not limited to the chamber referred to in the preferred embodiments. Any location where a gas dissociation degree measuring device is disposed is within the scope of the present invention. The preferred embodiments in the specifications are illustrated of the present invention rather than limiting of the present invention, citing devices for physical vapor deposition, chemical vapor deposition or etching in the semiconductor industry as examples.

DETAILED DESCRIPTION OF THE PREFERRED EMBODIMENTS

Figure 3:
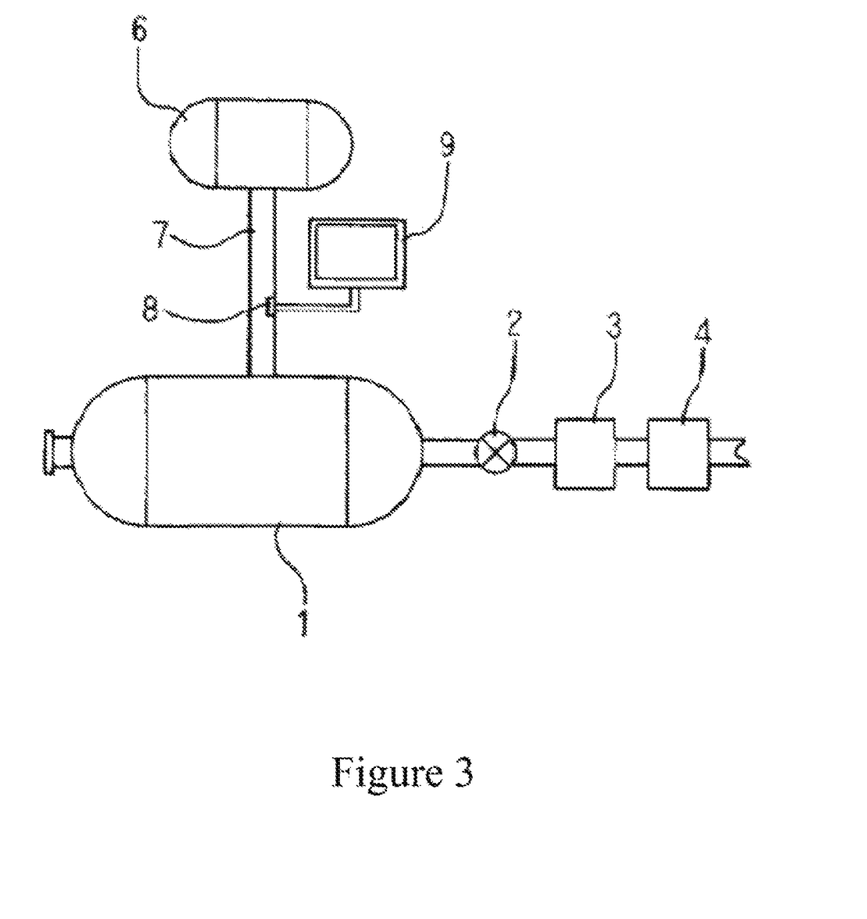
FIG. 3 is a structural drawing of the present invention.
Figure 4:
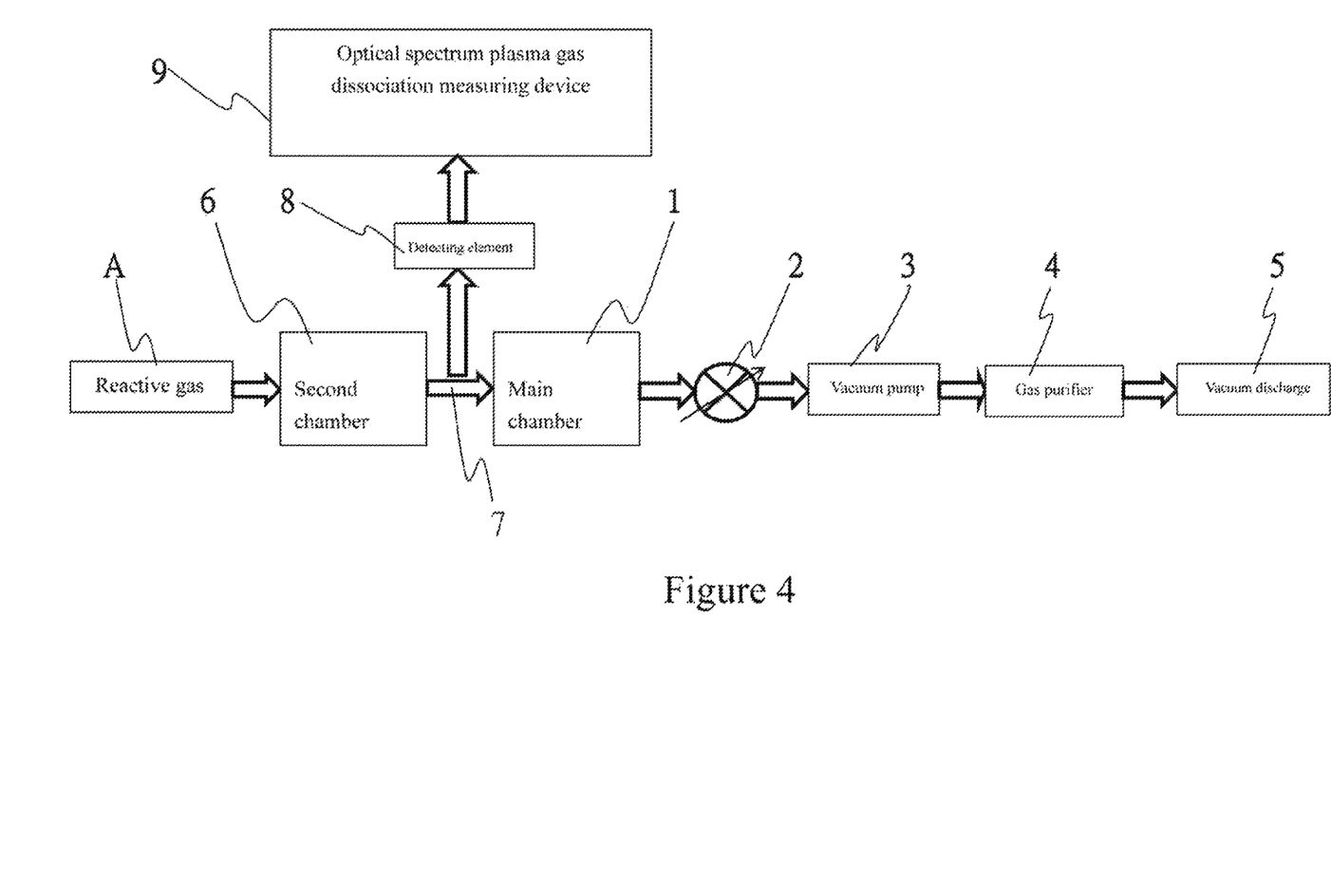
FIG. 4 is a block diagram showing the present invention installed at a location.

Please refer to both FIG. 3 and FIG. 4, showing respectively a structural drawing and a block diagram of the present invention. As the figures show, the present invention includes a main chamber 1 for storing gas in plasma state and a second chamber 6 connected to the main chamber 1. The main chamber 1 is provided for performing the processes of plasma-assisted deposition, membrane etching and material surface modification to achieve special functions and effects in semiconductor integrated circuit manufacturing. Connected to the main chamber 1 is a throttling valve 2, a vacuum pump 3 and a gas purifier 4. An appropriate amount of reactive gas A is discharged in the second chamber 6 according to the dissociation quantity value and passed through a tube body 7 to perform cleaning of the main chamber 1. Vacuum discharge 5 is then achieved through the vacuum pump 3 and gas purifier 4.

A combination of the foregoing components provides a method and a device for measuring gas dissociation degrees with an optical spectrometer. In a manufacturing process the gas dissociation degree in the second chamber 6 is detected by a detecting element 8 and the relative dissociation quantity value is calculated by an optical spectrum plasma gas dissociation measuring device 9. When the contamination value in the main chamber 1 is too high, an appropriate amount of reactive gas A is discharged and dissociated in the second chamber 6 according to the dissociation quantity value. The dissociated reactive gas A is then passed through the tube body 7 for removing contaminants in the main chamber 1 to facilitate the cleaning of the main chamber 1 at reduced labor and material costs.

Figure 8:
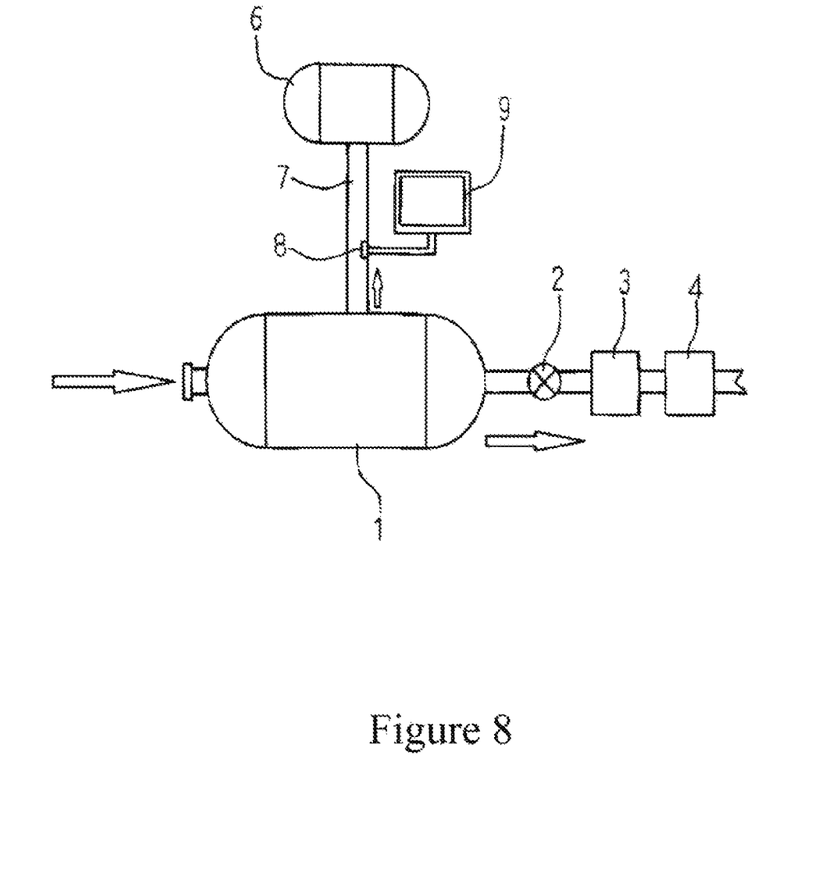
FIG. 8 is a drawing of the present invention in use.

Please refer to FIG. 4 and FIG. 8, showing respectively a block diagram of the present invention and a drawing of the present invention in use. As the figures show, when the present invention is in use, same as a conventional plasma gas device, an appropriate amount of reactive gas A is discharged in the second chamber 6 according to the dissociation quantity value. The dissociated reactive gas A is passed through the tube body 7 to perform a cleaning process in the main chamber 1. Vacuum discharge 5 is then achieved through the vacuum pump 3 and gas purifier 4.

Figure 9:
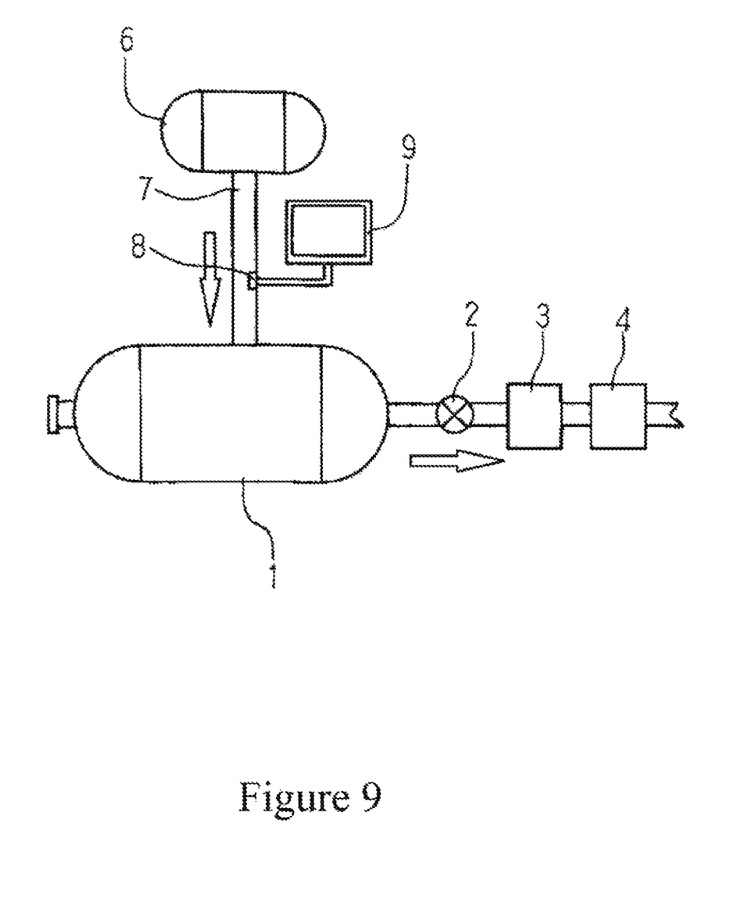
FIG. 9 is a drawing of the present invention performing a cleaning process

Please refer to FIG. 4 and FIG. 9, showing respectively a block diagram of the present invention and a drawing of the present invention performing a cleaning process. As the figures show, when the present invention operates over a period of time, the detecting element 8 constantly detects the gas dissociation degree (gas wavelength) in the second chamber 6, and the relative dissociation quantity value is calculated by the optical spectrum plasma gas dissociation measuring device 9. The relative dissociation quantity value is displayed and provided to a user. When the contamination value in the main chamber 1 is too high, the user may open the second chamber 6 and discharge an appropriate amount of reactive gas A in the second chamber 6 according to the dissociation quantity value that is calculated by the optical spectrum plasma gas dissociation measuring device 9. The reactive gas A is then passed through the tube body 7 to the main chamber 1 to perform cleaning of the main chamber 1. During the cleaning process, the optical spectrum plasma gas dissociation measuring device 9 may determine whether the plasma gas dissociation degree is sufficient for effective cleaning of the main chamber 1. Unlike a conventional plasma gas device, with a device according to the present invention there is no need to repeatedly place an integrated circuit wafer probe for testing to determine whether further cleaning is necessary. The cleaning of the main chamber 1 is therefore more efficient and effective at reduced labor and material costs.

Figure 5:
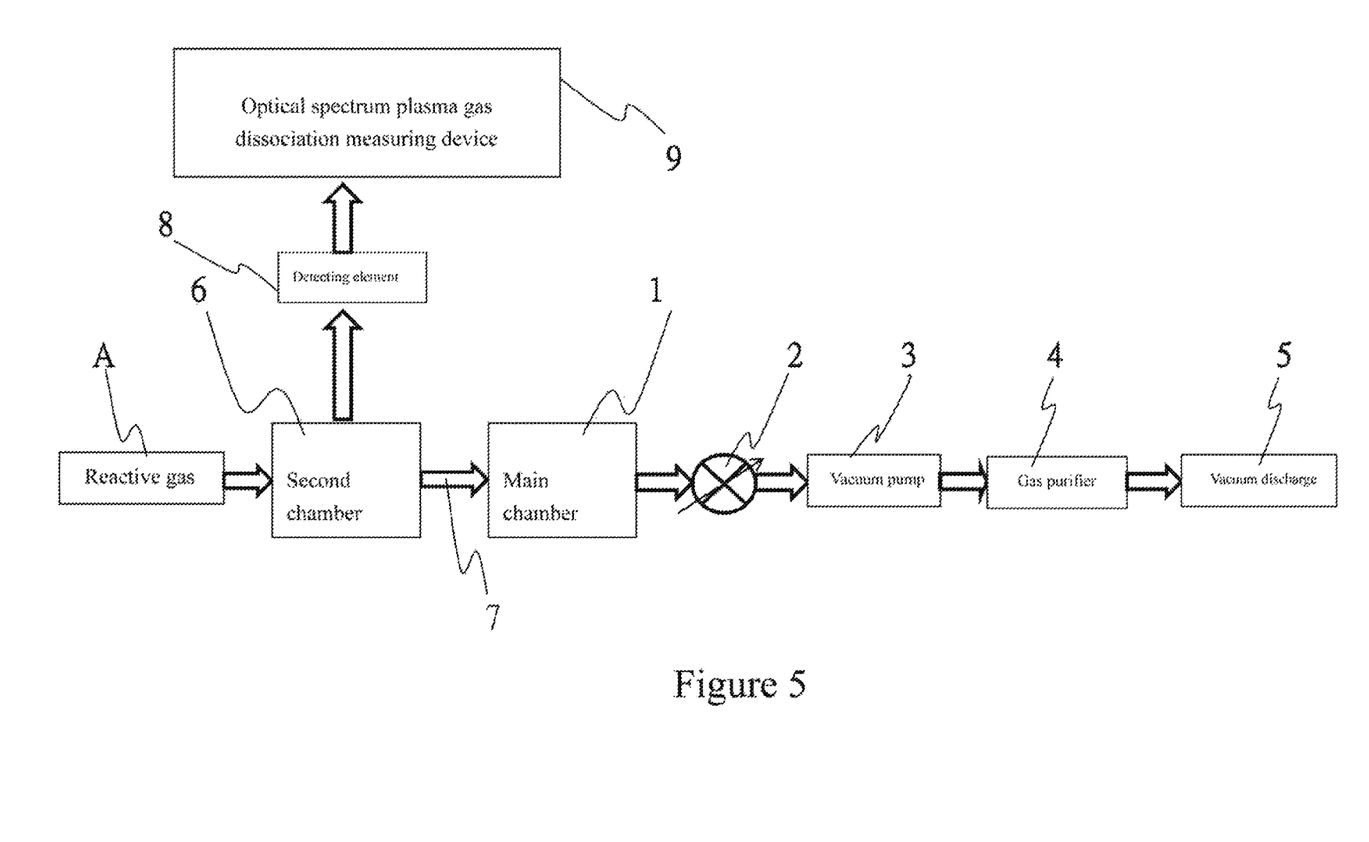
FIG. 5 is a block diagram showing the present invention installed at another location.

A first preferred embodiment of the present invention is a method and a device for measuring plasma gas dissociation degrees with an optical spectrometer, wherein, as shown in FIG. 5, the detecting element 8 and the optical spectrum plasma gas dissociation measuring device 9 are disposed at appropriate locations in the second chamber 6 to detect plasma gas dissociation degrees therein.

Figure 6:
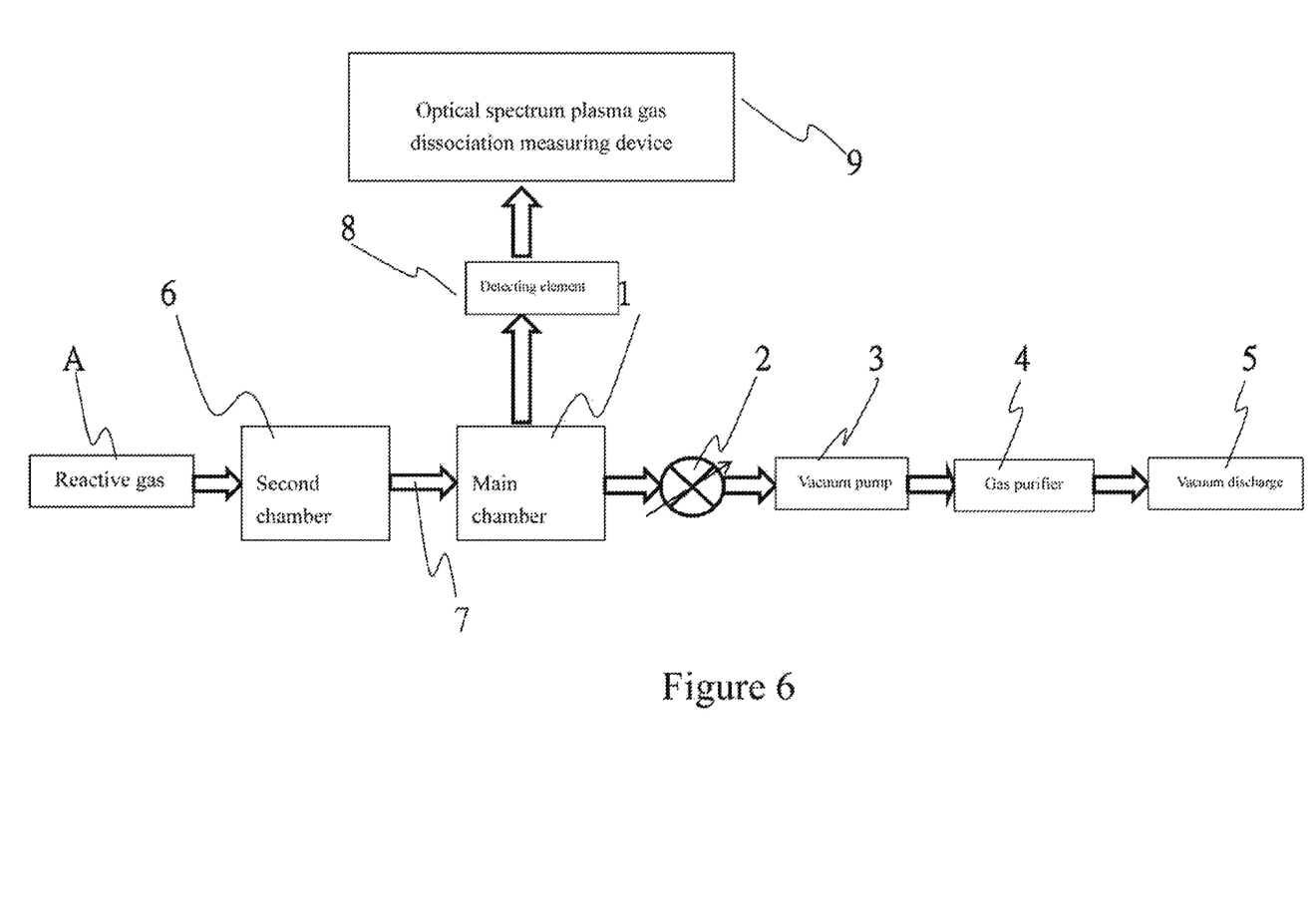
FIG. 6 is a block diagram showing the present invention installed at yet another location.
Figure 7:
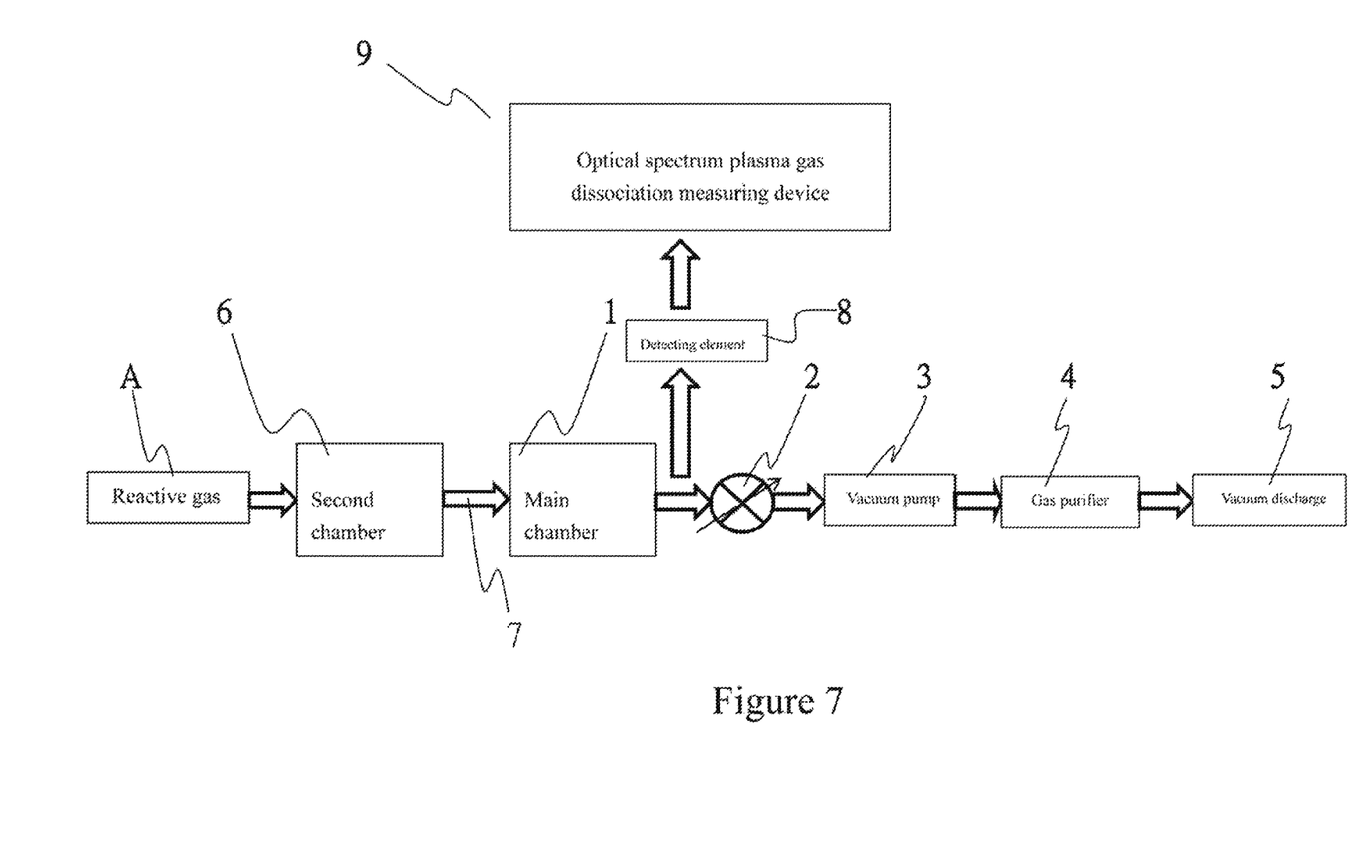
FIG. 7 is a block diagram showing the present invention installed at yet another location.

A second preferred embodiment of the present invention is a method and a device for measuring plasma gas dissociation degrees with an optical spectrometer, wherein, as shown in FIG. 6, the detecting element 8 and the optical spectrum plasma gas dissociation measuring device 9 are disposed at appropriate locations in the main chamber 1 to detect plasma gas dissociation degrees therein.

A third preferred embodiment of the present invention is a method and a device for measuring plasma gas dissociation degrees with an optical spectrometer, wherein the detecting element 8 and the optical spectrum plasma gas dissociation measuring device 9 are disposed at appropriate locations in the fluid path. They may also be disposed in any of the fluid paths as shown in FIG. 3 to detect dissociation degrees.

In view of the foregoing, in the present invention a second chamber 6 is connected to the main chamber 1 and a detecting element 8 and an optical spectrum plasma gas dissociation measuring device 9 are disposed between the main chamber 1 and the second chamber 6 to form a method and a device for measuring gas dissociation degrees with an optical spectrometer. The detecting element 8 detects the plasma gas dissociation degree in the tube body 8, and the relative dissociation quantity value is calculated. An appropriate amount of reactive gas A is discharged in the second chamber 6 according to the dissociation quantity value and passed through the tube body 7 to the main chamber 1 for removing contaminants in the main chamber 1 to facilitate the cleaning of the main chamber 1 at reduced labor and material costs.

Figure 1:
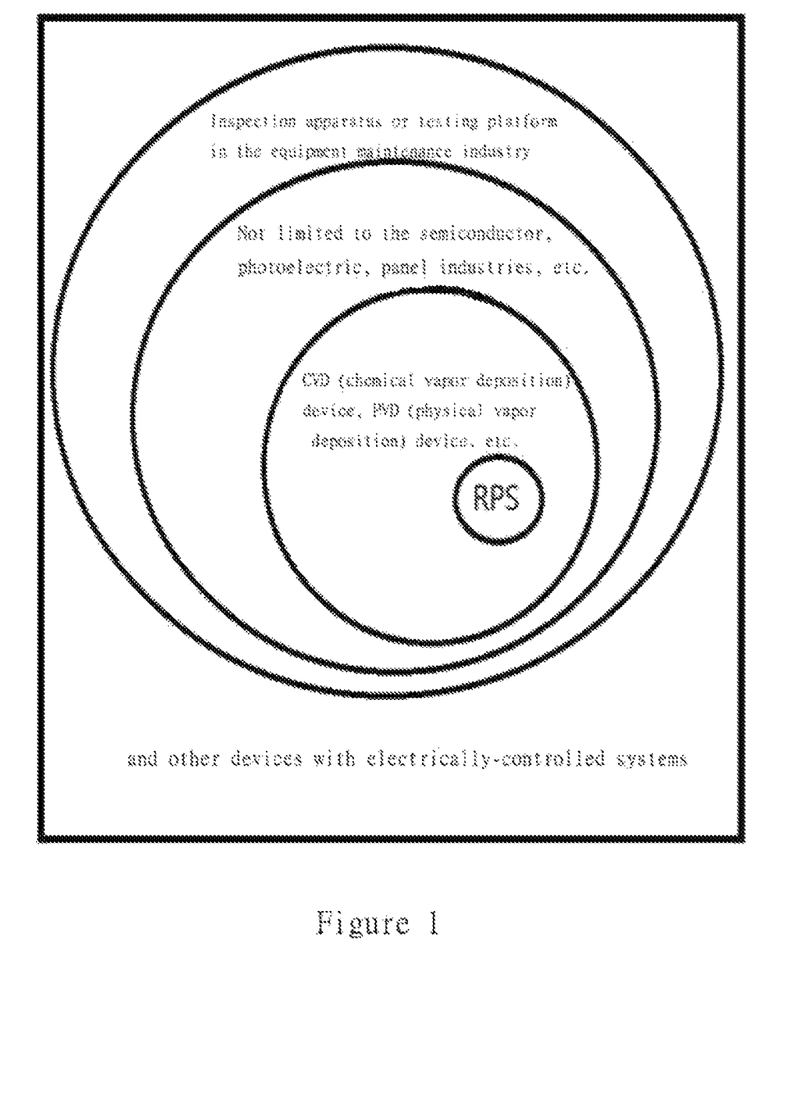
FIG. 1 shows relevant fields where the present invention may be applied.

The present invention may be applied in a wide range of fields, as shown in FIG. 1. A characteristic of the present invention is to provide a method and a device for measuring gas dissociation degrees, wherein the gas dissociation degree in a tube body is detected by a device according to the present invention and the relative dissociation quantity value is calculated to serve as a reference for choosing among various corresponding handling methods. For example, an appropriate amount of dissociated reactive gas may be discharged to remove contaminants in a primary path of gas to achieve efficient and effective cleaning. The present invention may be applied to any device and/or any apparatus that requires measuring of gas dissociation degrees, including but not limited to physical vapor deposition device, chemical vapor deposition device, etching device and any other relevant device in the semiconductor, photoelectric, panel industries and any other relevant industry. The present invention may also be directly disposed in a remote plasma source device. Further, the present invention may also be applied in any inspection examination device in the biotechnology, chemistry, applied physics industries and any other relevant industry. Still further, the present invention may also be applied to any inspection apparatus or testing platform in the equipment maintenance industry for any of the foregoing industries (referring to FIG. 1).

The preferred embodiments are only illustrated of one of the methods and devices for measuring dissociation according to the present invention rather than limiting of the present invention. Any optical spectrum dissociation measuring device disposed in any location where dissociation may take place, including but not limited to a chamber, as well as any optical spectrum dissociation measuring device applied in physical vapor deposition device, chemical vapor deposition device, etching device and any other relevant device in the semiconductor, photoelectric, panel industries and any other relevant industry and any optical spectrum dissociation measuring device directly disposed in a remote plasma source device are all within the spirit and scope of the appended claims. The present invention is intended to cover various modifications and changes included within the spirit and scope of the appended claims, the scope of which should be accorded the broadest interpretation so as to encompass all such modifications and similar structures.

What is claimed is:

1. A device for measuring gas dissociation degrees, comprising:
   a main path for performing processes of plasma-assisted deposition, membrane etching and material surface modification to achieve special functions and effects in semiconductor integrated circuit manufacturing;
   a second path connected to the main path for storing reactive gas;
   a detecting element and an optical spectrum plasma gas dissociation measuring device disposed between the main path and the second path, wherein the detecting element detects a gas dissociation degree and the optical spectrum plasma gas dissociation measuring device calculates a relative dissociation quantity value.

2. A device for measuring gas dissociation degrees with an optical spectrometer of claim 1, wherein the main path and the second path are connected with a tube body and the detecting element and optical spectrum plasma gas dissociation measuring device are disposed at appropriate locations in the tube body.

3. A device for measuring gas dissociation degrees with an optical spectrometer of claim 1, wherein the detecting element and optical spectrum plasma gas dissociation measuring device are disposed at appropriate locations in the main path.

4. A device for measuring gas dissociation degrees with an optical spectrometer of claim 1, wherein the detecting element and optical spectrum plasma gas dissociation measuring device are disposed at appropriate locations in the second path.

5. A device for measuring gas dissociation degrees with an optical spectrometer of claim 1, wherein the detecting element and optical spectrum plasma gas dissociation measuring device are disposed at appropriate locations in the fluid path.

6. A device for measuring gas dissociation degrees with an optical spectrometer of claim 1, wherein the detecting element and optical spectrum plasma gas dissociation measuring device may be applied in a device in a plasma source device, a plasma gas chamber or an electrical control system.

7. A device for measuring gas dissociation degrees with an optical spectrometer of claim 1, wherein the processes comprise processes in a physical vapor deposition device, chemical vapor deposition device, etching device and in the semiconductor, photoelectric, panel industries, a remote plasma source device, and inspection examination device in the biotechnology, chemistry, applied physics industries, and inspection apparatus or testing platform in the equipment maintenance industry for the foregoing industries.

8. A method for measuring gas dissociation degrees, comprising:
   performing a reaction process with at least one reactive gas in a main path and a second path connecting to the main path for storing the reactive gas;
   detecting a plasma gas dissociation degree of the reactive gas in the reaction process;
   calculating a dissociation quantity value of the reactive gas in the reaction process;
   providing an amount of the reactive gas in the main path after the reaction process according to the dissociation quantity value of the reactive gas; and
   discharging the reactive gas for removing contaminants in the main path.

9. The method of claim 8, wherein the reaction process comprises physical vapor deposition, chemical vapor deposition, and etching processes.

10. The method of claim 8, wherein the plasma gas dissociation degree of the reactive gas is detected by a detecting element and the dissociation quantity value of the reactive gas is calculated by an optical spectrum plasma gas dissociation measuring device.

11. The method of claim 10, wherein the detecting element and the optical spectrum plasma gas dissociation measuring device are disposed at the main path.

12. The method of claim 10, wherein the detecting element and the optical spectrum plasma gas dissociation measuring device are disposed at the second path.

13. The method of claim 8 further comprising a step of vacuum discharge after the step of discharging the reactive gas by a vacuum pump and a gas purifier connecting to the main path.

14. The method of claim 13, wherein the detecting element and the optical spectrum plasma gas dissociation measuring device are disposed between the main path and the vacuum pump.

* * * * *